US 6,552,796 B2

(12) United States Patent
Magnin et al.

(10) Patent No.: US 6,552,796 B2
(45) Date of Patent: Apr. 22, 2003

(54) APPARATUS AND METHOD FOR SELECTIVE DATA COLLECTION AND SIGNAL TO NOISE RATIO ENHANCEMENT USING OPTICAL COHERENCE TOMOGRAPHY

(75) Inventors: Paul Magnin, Andover, MA (US); John W. Goodnow, Arlington, MA (US); Christopher L. Petersen, Carlisle, MA (US); Joseph Schmitt, Andover, MA (US)

(73) Assignee: LightLab Imaging, LLC, Westford, MA (US)

( * ) Notice: Subject to any disclaimer, the term of this patent is extended or adjusted under 35 U.S.C. 154(b) by 0 days.

(21) Appl. No.: 09/826,897

(22) Filed: Apr. 6, 2001

(65) Prior Publication Data

US 2002/0163622 A1 Nov. 7, 2002

(51) Int. Cl.⁷ .................................................. G01B 9/02
(52) U.S. Cl. ...................................................... 356/450
(58) Field of Search ................................ 356/345, 73.1, 356/346, 351, 357, 360, 356, 358, 355, 359, 354, 349, 450; 250/227.27, 227.19; 351/206, 209, 221, 227, 243, 211, 205, 219, 212

(56) References Cited

U.S. PATENT DOCUMENTS

| 3,776,637 A | 12/1973 | Hecht |
| 4,179,219 A | 12/1979 | Smith |
| 4,468,747 A | 8/1984 | Leavitt et al. |
| 4,471,449 A | 9/1984 | Leavitt et al. |
| 5,007,721 A | 4/1991 | Morris et al. |
| 5,033,853 A | 7/1991 | Frangineas, Jr. |
| 5,062,150 A | 10/1991 | Swanson et al. |
| 5,195,521 A | 3/1993 | Melton, Jr. et al. |
| 5,321,501 A | 6/1994 | Swanson et al. |
| 5,387,969 A | 2/1995 | Marantette |
| 5,459,570 A | 10/1995 | Swanson et al. |
| 5,465,147 A | 11/1995 | Swanson |
| 5,491,524 A | 2/1996 | Hellmuth et al. |
| 5,619,368 A | 4/1997 | Swanson |
| 5,748,598 A | 5/1998 | Swanson et al. |
| 5,751,419 A | 5/1998 | Takahashi et al. |
| 5,784,352 A | 7/1998 | Swanson et al. |
| 5,892,583 A | 4/1999 | Li |
| 5,994,690 A | 11/1999 | Kulkarni et al. |
| 6,002,480 A * | 12/1999 | Izatt et al. .................. 356/479 |
| 6,069,698 A * | 5/2000 | Ozawa et al. ............... 356/511 |
| 6,106,465 A | 8/2000 | Napolitano et al. |
| 6,111,645 A | 8/2000 | Tearney et al. |
| 6,191,862 B1 * | 2/2001 | Swanson et al. ............ 356/450 |

OTHER PUBLICATIONS

Takada, Kazumasa, et al., "New Measurement System for Fault Location in Optical Waveguide Devices Based on an Interferometric Technique," *Applied Optics*, vol. 26(9), 1987, pp. 1603–1606 (reprinted pp. 115–118).

(List continued on next page.)

Primary Examiner—Marvin M. Lateef
Assistant Examiner—John R. Sanders
(74) Attorney, Agent, or Firm—Fleshner & Kim, LLP

(57) ABSTRACT

Methods and apparatuses are provided for performing optical imaging on a sample. The method and apparatuses continually adjust the path-length of a reference arm or data acquisition in a manner such that imaging information is obtained only from a longitudinal range that contains a selective portion of a sample from which imaging information is to be obtained. The apparatuses include a starting point adjustment device that determines a point with respect to a sample at which imaging information collection is to be started. A controller then controls a second scanning mechanism, in addition to a first scanning mechanism, such that imaging information is obtained only from a longitudinal range that contains a selective portion of a sample from which imaging information is to be obtained. In this way, the amount of data collected can be reduced to that within the area of interest.

38 Claims, 8 Drawing Sheets

OTHER PUBLICATIONS

Huang, David, et al., "Optical Coherence Tomography," *Science*, vol. 254, 1991, pp. 1178–1181.

Swanson, E.A., et al., "Optical Coherence Tomography Principles, Instrumentation, and Biological Applications," *Biomedical Optical Instrumentation and Laser-Assisted Biotechnology*, Kluwer Academic Publishers, 1996, pp. 291–303.

Brezinski, Mark E., et al., "Optical Coherence Tomography for Optical Biopsy," *Circulation*, vol. 93, 1996; pp. 1206–1213.

Ballif, J., et al., "Rapid and Scalable Scans at 21 m/s in Optical Low-Coherence Reflectometry," *Optics Letters*, vol. 22(11), 1997, pp. 757–759 (reprinted pp. 340–352).

Tearney, G.J., et al., "Optical Biopsy in Human Gastrointestinal Tissue Using Optical Coherence Tomography," *The American Journal of Gastroenterology*, vol. 92, No. 10, 1997.

Tearney, Guillermo J., et al., "In Vivo Endoscopic Optical Biopsy with Optical Coherence Tomography," *Science*, vol. 276, 1997.

Szydlo, J., et al., "Air-Turbine Driven Optical Low-Coherence Reflectometry at 28.6-kHz Scan Repetition Rate," *Optics Communications*, vol. 154, 1998, pp. 1–4 (reprinted pp. 349–352).

* cited by examiner

APPARATUS AND METHOD FOR SELECTIVE DATA COLLECTION AND SIGNAL TO NOISE RATIO ENHANCEMENT USING OPTICAL COHERENCE TOMOGRAPHY

BACKGROUND OF THE INVENTION

1. Field of the Invention

The invention is directed to an apparatus and method for selective data collection and/or utilization using optical coherence tomography. In particular, the invention is directed to an apparatus and method of collecting and/or utilizing, using optical coherence tomography, only that imaging information relevant to a particular medical diagnosis/assessment.

2. Background of the Related Art

Optical coherence tomography (OCT) is a relatively new imaging modality with the ability to perform high resolution, high-sensitivity, cross sectional imaging of microstructures. OCT has several significant advantages over ultrasound and other established imaging techniques. First, OCT can directly measure cross-sectional microstructure on a micron scale. Second, OCT can perform imaging of structures in situ and without contact. Third, imaging can be performed in real time, and fourth, because OCT technology is based on fiber optics, it can be interfaced with a wide range of medical, microscopic, and industrial instruments.

The operating principle of OCT is analogous to that of ultrasound B-mode imaging, except OCT uses light rather than sound and performs imaging by measuring the intensity of light backscattered from a sample being imaged. OCT produces two-, or three-dimensional images by directing an optical beam at an object, and measuring backscattered light as the beam is scanned across the object. An OCT image is a gray scale or false color two-dimensional representation of backscattered light intensity in a cross-sectional plane.

In medical imaging, the OCT image represents the differential backscattered contrast between different tissue types on a micron scale. Using infrared light, state-of-the-art OCT imaging systems can achieve resolutions approximately 5–25× higher than other imaging modalities used in clinical medicine.

There are a variety of interferometric embodiments of OCT systems. For example, one typical implementation uses a fiber optic coupler as the basis of a Michelson interferometer. One of the arms of the interferometer delivers and scans the optical beam on a sample, while the other arm functions as a reference arm with a high-speed longitudinal scanning mechanism. When the optical path-length to a reflection site within the sample matches the path-length in the reference arm, coherent optical interference occurs at the photodetector. The interference signal is detected, demodulated, processed, stored and/or displayed to yield the backscattered light intensity versus depth for a given transverse or angular position of the incident beam. Examples of OCT systems are taught in copending application Ser. No. 09/233,421 [Attorney Docket No. CDT-01] and U.S. Pat. Nos. 5,321,501, 5,459,570, and 6,111,645, which are hereby incorporated by reference.

OCT imaging can be performed non-invasively and in real time over approximately the same depth over which tissue is removed in a biopsy. Thus, OCT can be used in applications where conventional biopsies are impractical or impossible.

A tremendous amount of data is collected during OCT imaging because of the high resolution of the modality. The large amount of raw data that makes up the image or series of images in a cine-loop can cause a data storage problem, as well as a real-time scan conversion problem. In addition, the signal-to-noise ratio in a well designed OCT system is limited by the number of photons the imaging probe can collect for each pixel in the resultant image.

The references discussed within this disclosure are incorporated by reference where appropriate for appropriate teachings of additional or alternative details, features and/or technical background.

SUMMARY OF THE INVENTION

An object of the invention is to solve at least the above problems and/or disadvantages and to provide at least the advantages described hereinafter.

Another object of the invention is to solve the above problems and/or disadvantages by improving the data efficiency of OCT systems. For a given light source, the number of photons collected in each image pixel can be increased by allowing more photon collection time per pixel. All other things being equal, this can be achieved by scanning fewer pixels in the image.

Another object of the invention is to increase the signal-to-noise ratio of OCT images.

A further object of the invention is to decrease the data processing and storage needs of an OCT system.

A still further object of the invention is to allow for higher frame rates given the same signal-to-noise ratio as conventional OCT systems.

Another object of the invention is to allow for higher line densities given the same signal-to-noise ratio as conventional OCT systems.

These and other advantages can be accomplished by methods and apparatuses for performing optical imaging on a system that continually adjusts the path-length of the reference arm in a manner that keeps the desired region of interest of an image within a restricted range of an OCT system. According to methods and apparatuses described herein, the path-length can be adjusted either manually by the operator or automatically according to a programmed algorithm.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

Figure 2A:
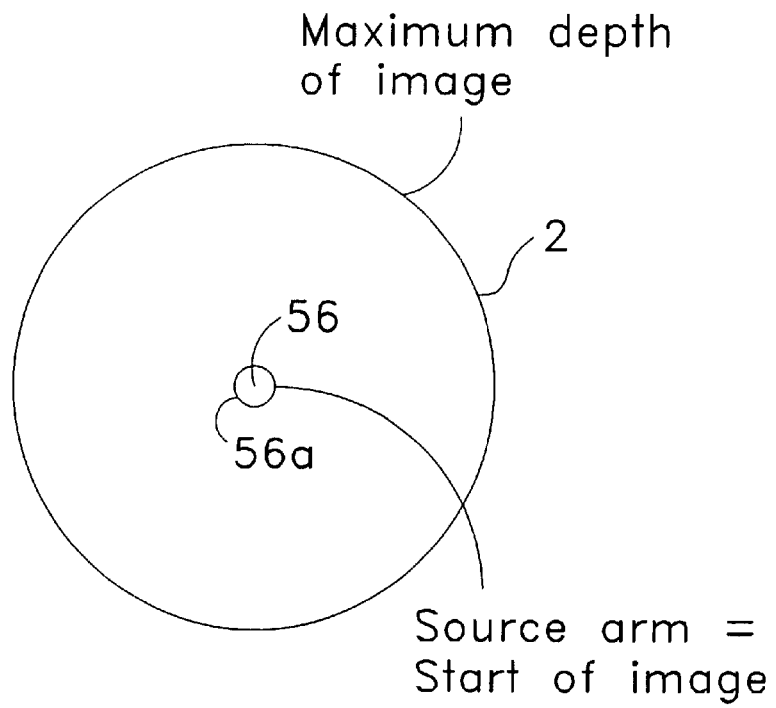
Figure 2B:
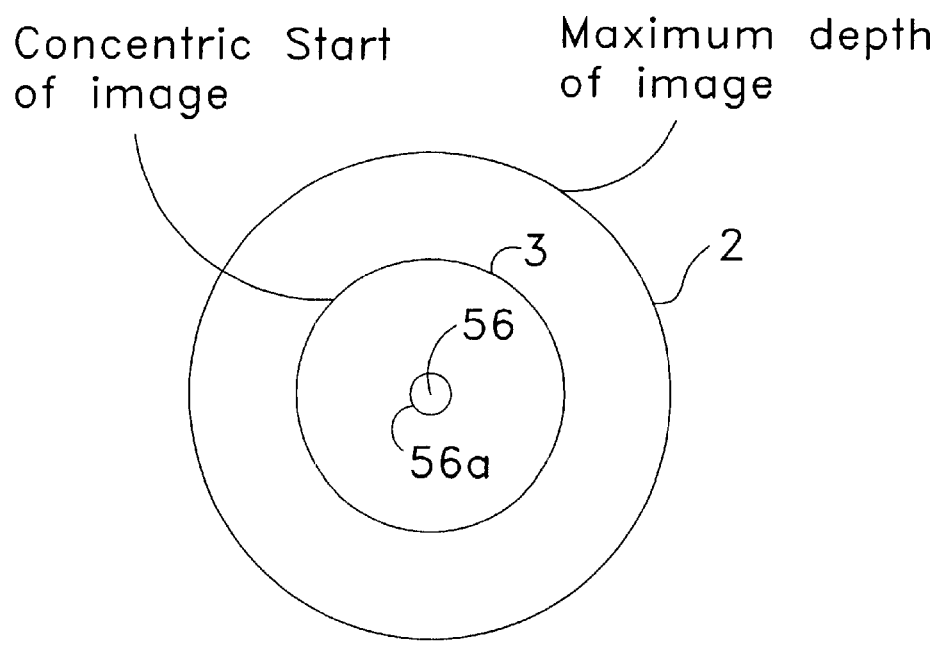
Figure 2C:
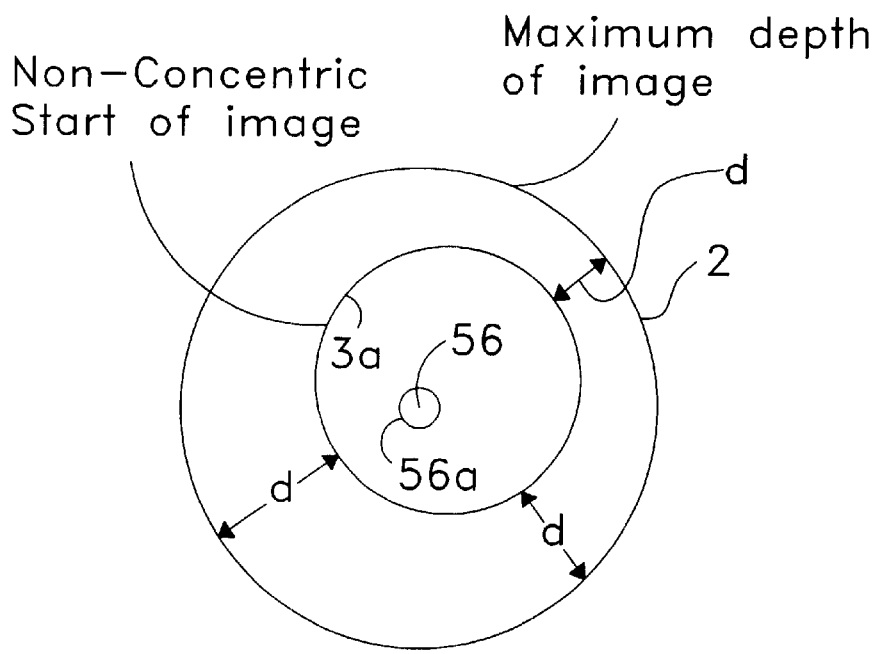
Figure 2D:
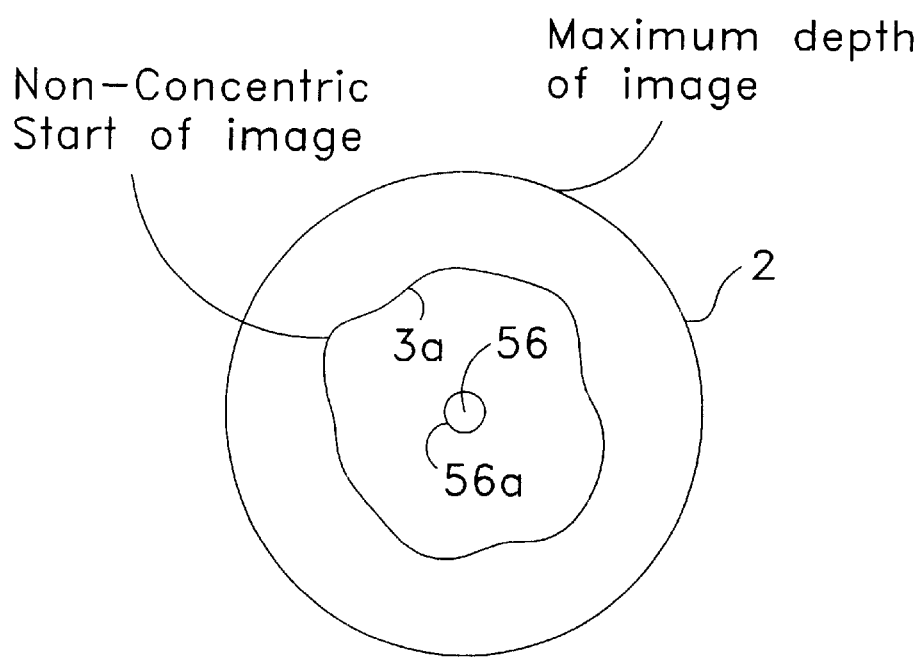
Figure 3:
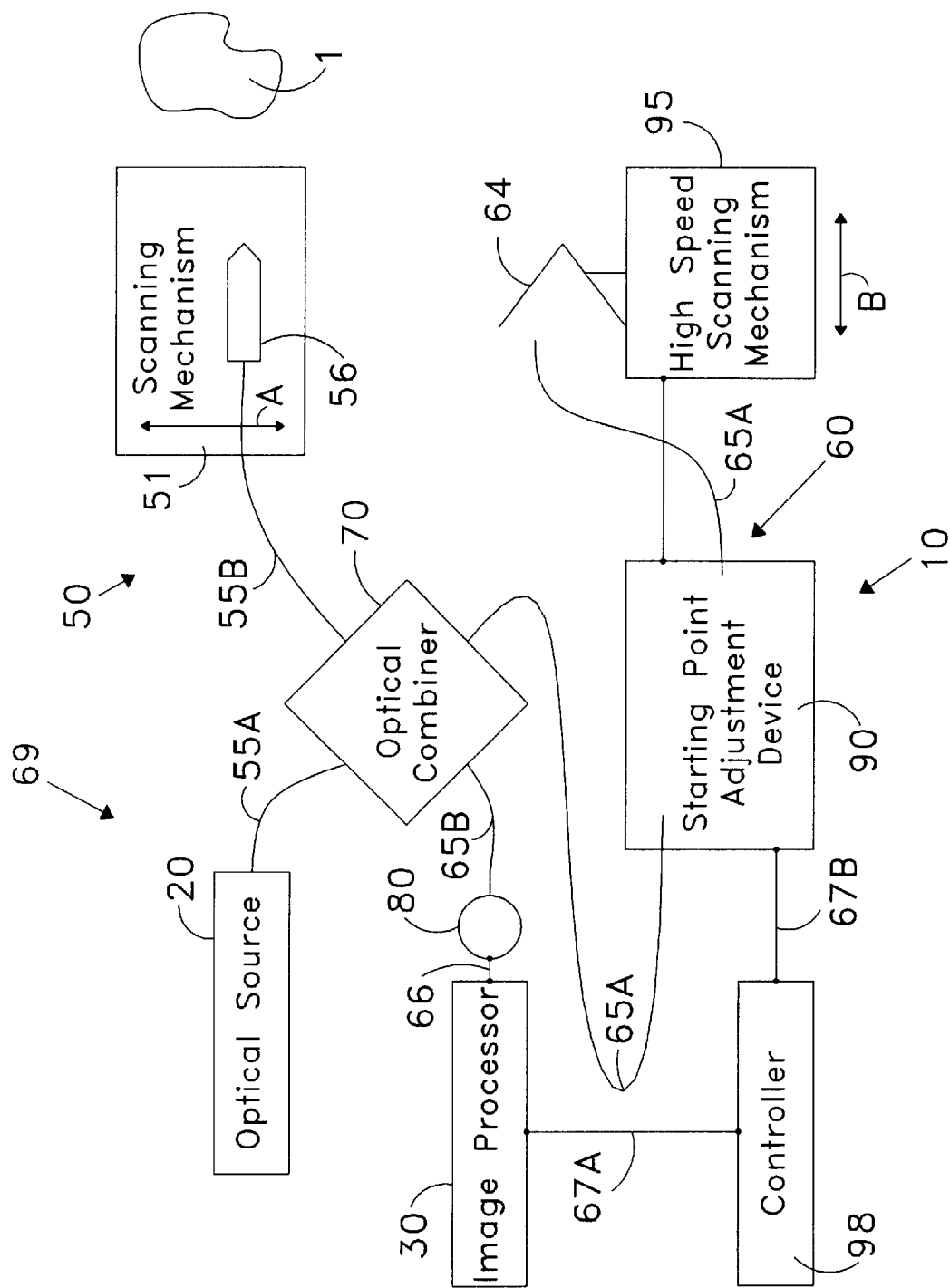
Figure 3A:
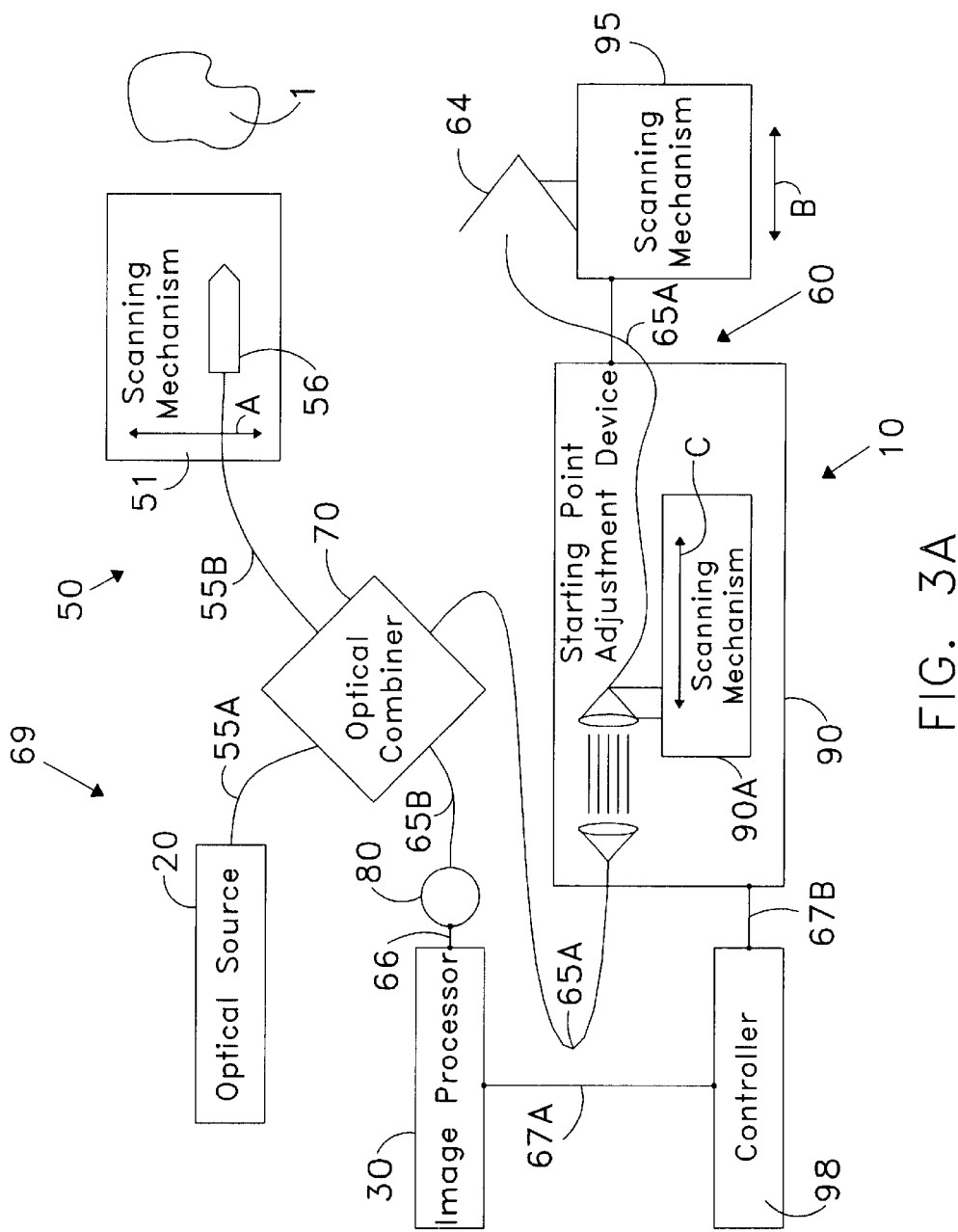
Figure 3B:
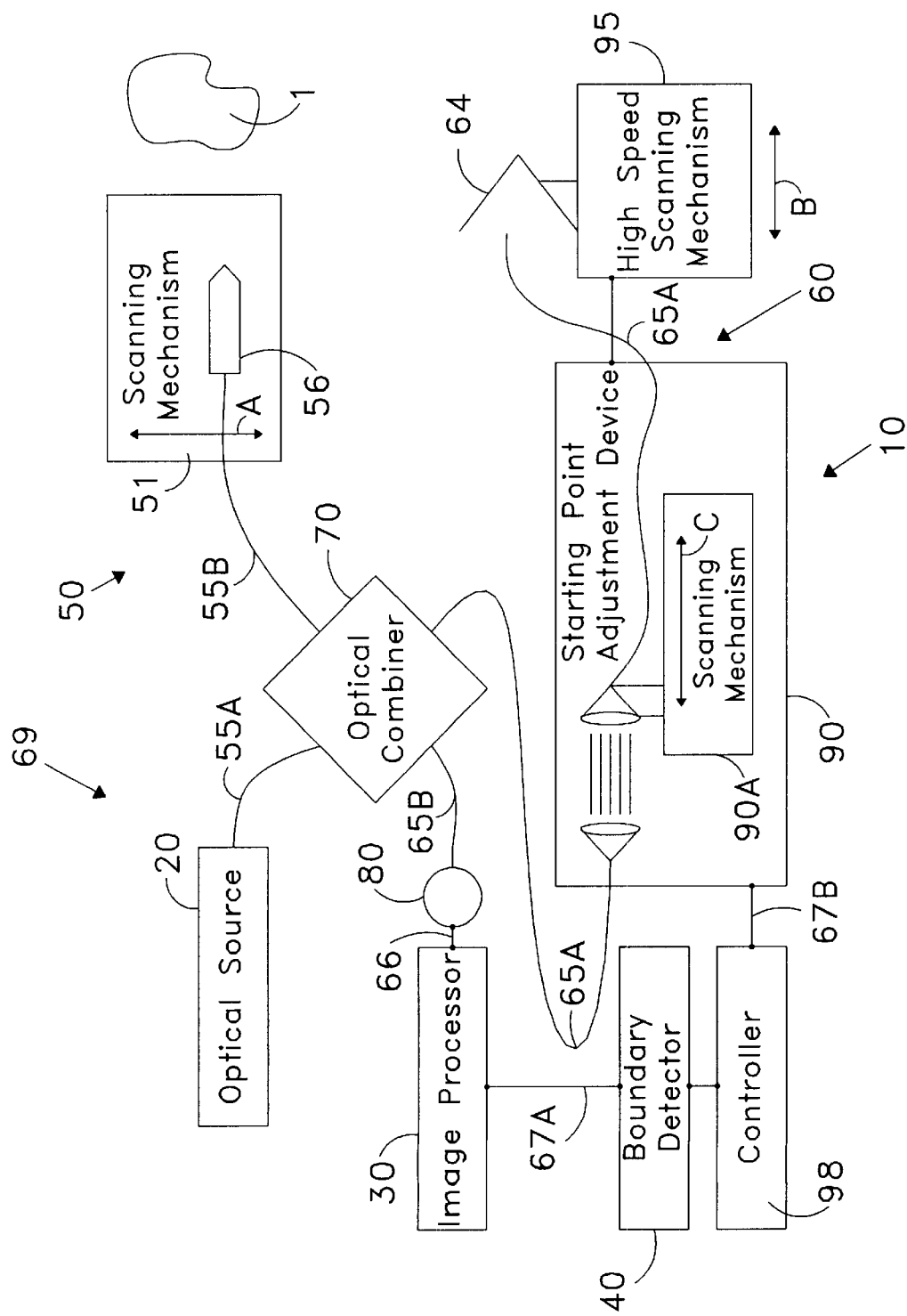
Figure 4:
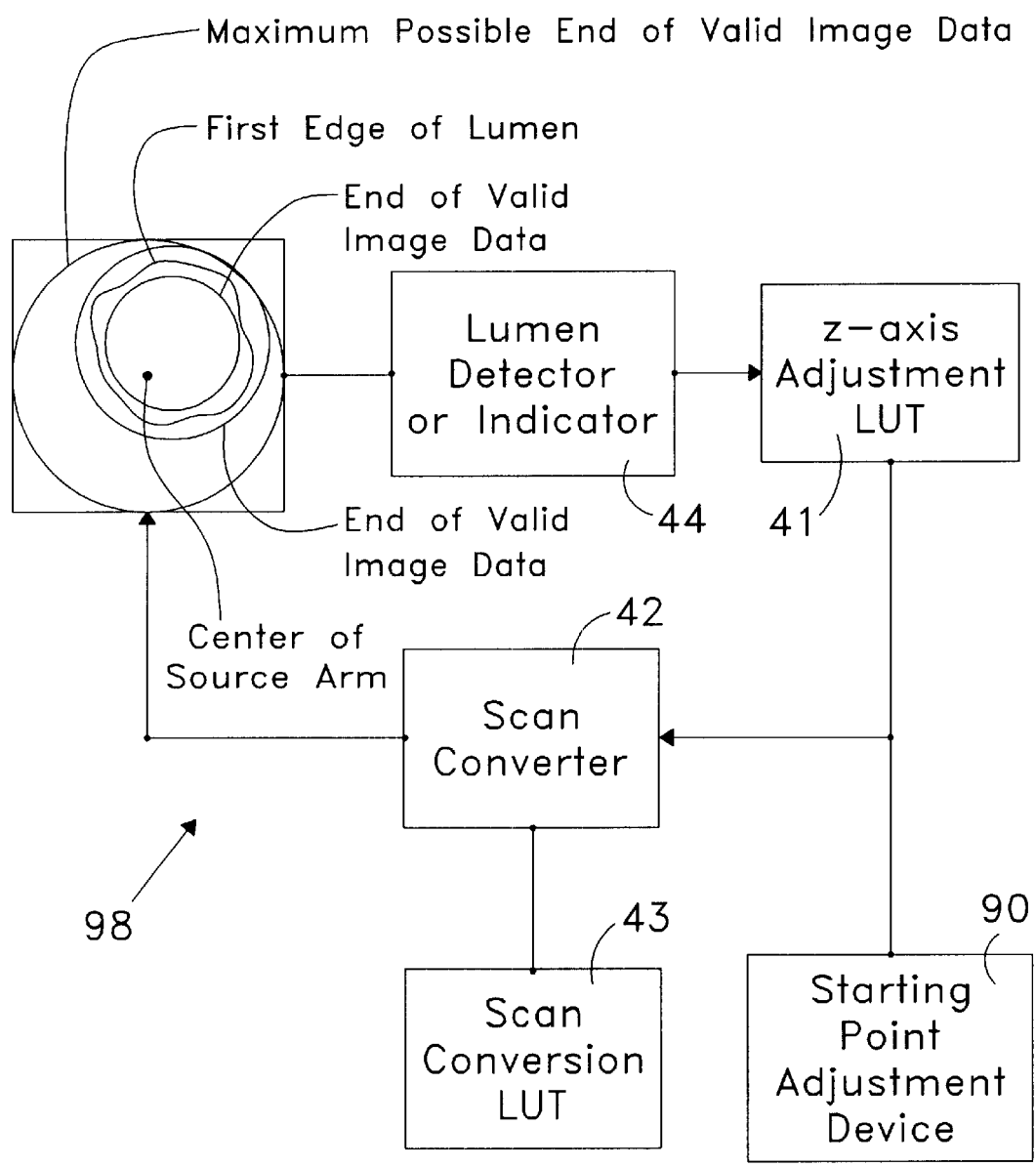
Figure 5:
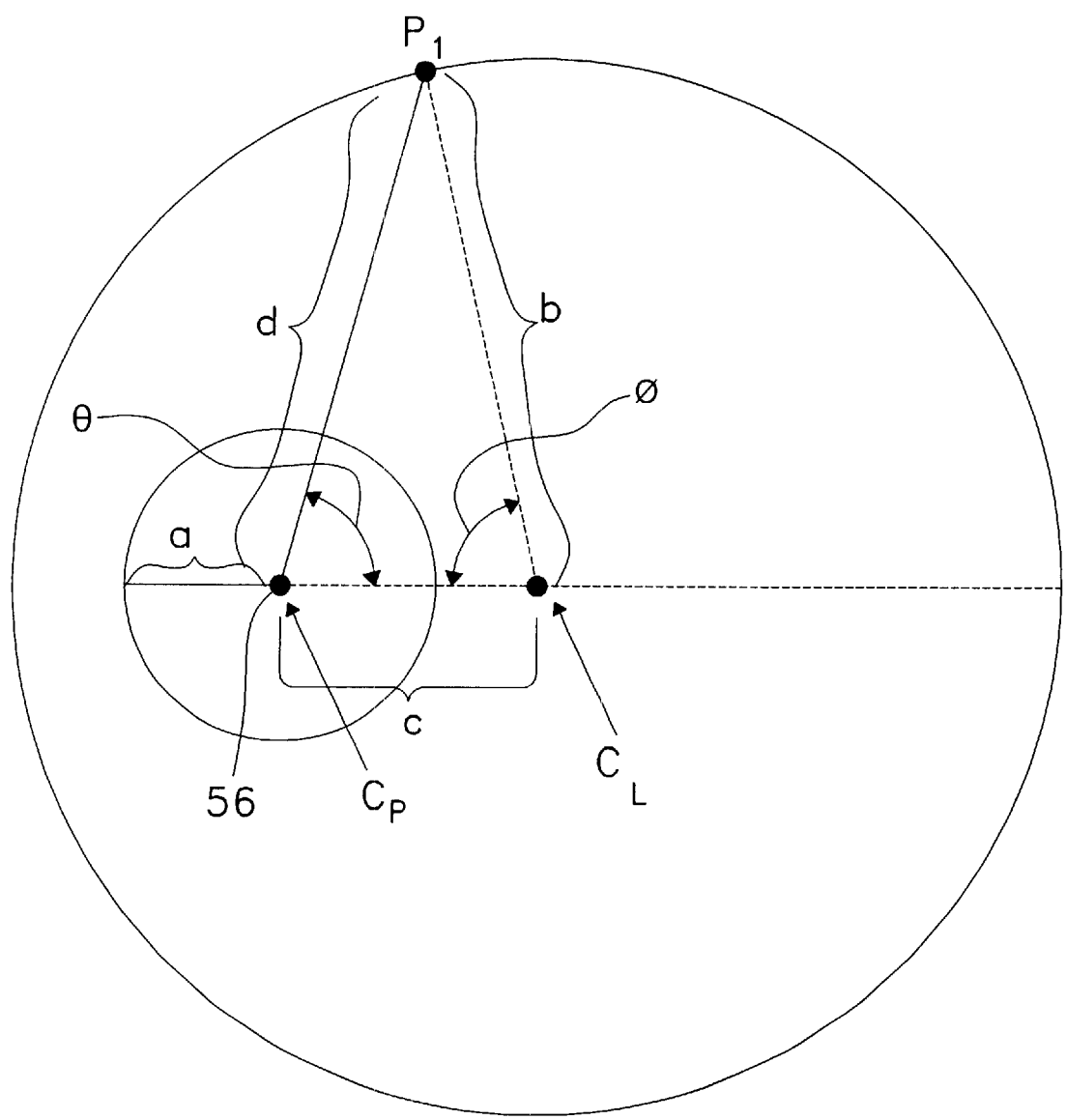

to FIG. 2A is a schematic drawing of an image generated by a conventional OCT system that employs a rotatable probe;

FIGS. 2B–2D are schematic drawings of images generated by an OCT imaging system according to the present invention;

FIG. 3 is a schematic drawing of an OCT imaging system according to an embodiment of the present invention;

FIG. 3A is a schematic drawing of an OCT imaging system according to another embodiment of the present invention;

FIG. 3B is a schematic drawing of an OCT imaging system according to another embodiment of the present invention;

FIG. 4 is a schematic drawing of a control system for an OCT imaging system according to an embodiment of the present invention; and FIG. 5 is an exemplary diagram demonstrating the variables input into equations for determining a reference arm offset as a function of probe rotation angle according to the invention.

DETAILED DESCRIPTION OF PREFERRED EMBODIMENTS

Figure 1:
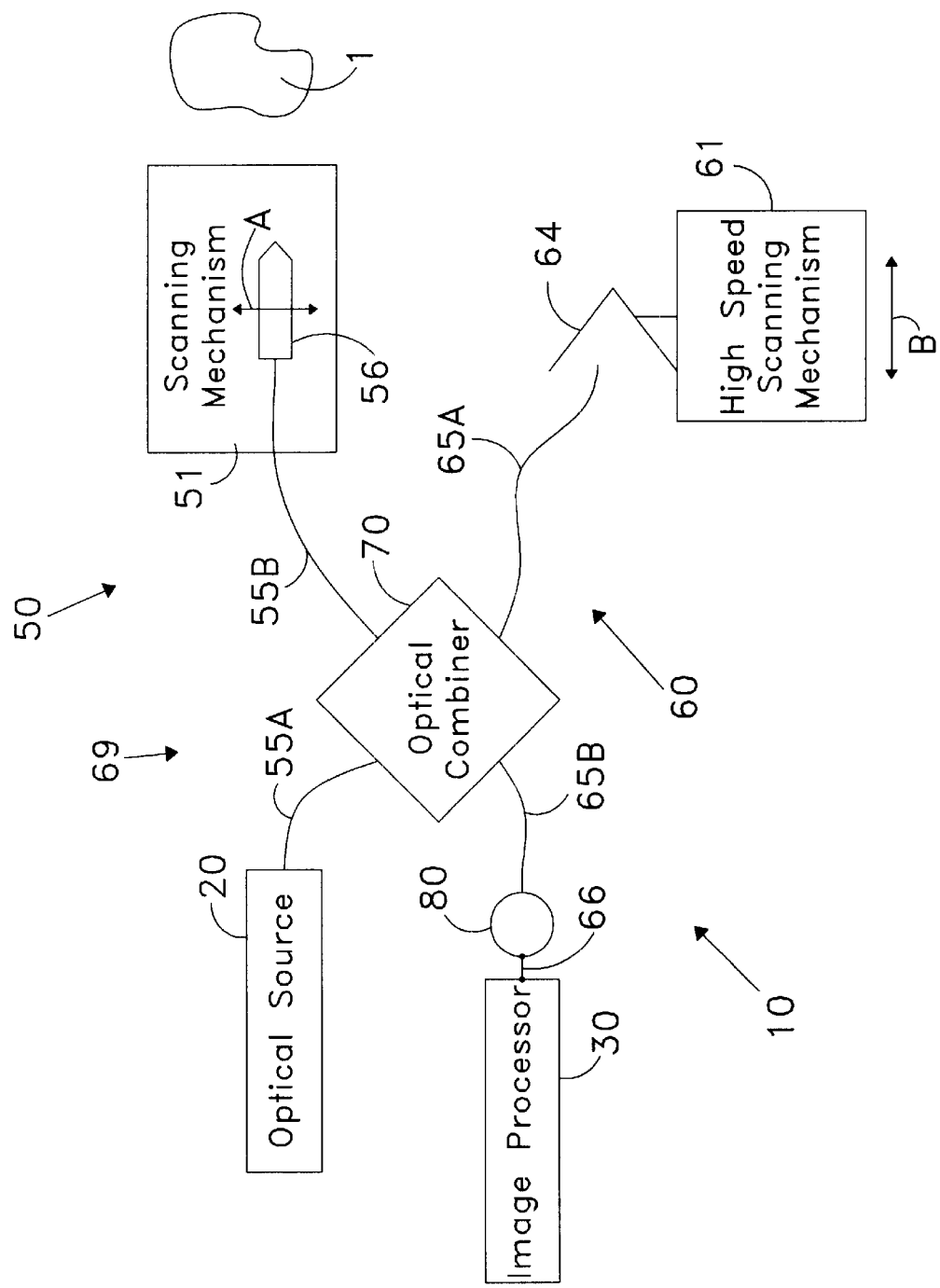
FIG. 1 is a schematic drawing of a conventional OCT imaging system.

An example of a conventional OCT system is shown in FIG. 1. The OCT system 10 includes an optical source 20, for example, a broadband light source, that provides a collimated or substantially collimated optical beam to a source arm 50 via a first optical path 55A and 55B. The source arm 50 delivers the optical beam to a sample 1, for example, tissue. The optical source 20 also provides the optical beam to the reference arm 60 via the first optical path 55A and a second optical path 65A.

The OCT system further includes an interferometer 69 that includes a sample optical path and a reference optical path together with an optical combiner 70. The sample optical path includes the path traveled by a portion of photons from the optical source 20 along the first optical path 55A through optical combiner 70 (which serves as both a splitter and combiner), then along the first optical path 55B through a scanning mechanism 51 to sample 1, for example, tissue, then back along first optical path 55B through optical combiner 70 along the second optical path 65B to detector 80. The reference optical path includes the path traveled by a second portion of photons from optical source 20 along the first optical path 55A through optical combiner 70, then along the second optical path 65A to reference reflector 64, then back along the second optical path 65A through optical combiner 70 along the second optical path 65B to detector 80.

The source arm 50 may terminate in the form of, for example, a probe, probe assembly, rotary coupler, catheter, guidewire, endoscope, laparoscope or microscope, designated by reference numeral 56 in FIG. 1. Examples of probe configurations that may be utilized are taught in U.S. Pat. No. 5,321,501, which is hereby incorporated by reference. For purposes of the following discussion, element 56 will be referred to as a probe assembly. The probe assembly may be rotatable. Further, the probe could be configured to be introduced into a bounded area of tissue, such as a blood vessel, or other bodily orifice.

The scanning mechanism 51 provides lateral movement to scan the length or width of the sample 1, the scanning movement represented by arrow A in FIG. 1. That is, the scanning mechanism 51 controls the position on the sample at which imaging is being performed by varying the position of the probe assembly 56. Alternatively, the sample can be moved to provide the scanning.

The reference arm 60 may comprise a scanning mechanism 61, for example, a high speed scanning mechanism such as a galvanometer, and a reflector 64. The reflector 64 may be, for example, a movable mirror, or corner reflector. The arrow B in FIG. 1 represents the scanning movement of the scanning mechanism 61.

When the path lengths to the sample 1 and the reflector 64 are matched, optical interference occurs at the optical combiner 70. The interference signal is detected by the photodetector 80. An electrical path 66 connects the photodetector 80 to an image processor 30. The interference signal is demodulated, processed, and is stored and/or displayed by the image processor 30.

In operation, the probe assembly 56 may be introduced into a bounded area of tissue, such as a blood vessel, or other body orifice. The optical source 20 delivers the optical beam to the probe assembly 56. The probe assembly 56 delivers the optical beam to the sample 1. The probe assembly 56 may be rotated, either automatically or manually. Further, the probe assembly may be rotated approximately 360° to deliver the optical beam in a complete circumferential sweep. The coherent portion of the optical beam penetrates the sample 1 to a maximum depth. This maximum depth determines the maximum depth of the image. The scanning mechanism 51 moves the source arm 50 to provide scanning of the full length or width of the sample 1, or alternately, may be configured to move the sample 1.

At the same time, the optical source 20 delivers the optical beam to the reference arm 60 via the first and second optical paths 55A, 65A. The optical beam reflects off reflector 64, which is moved by the scanning mechanism 61. When the path lengths to the sample 1 and to the reflector 64 are matched, that is, when they are within a coherence length of the optical beam, optical interference occurs at the optical combiner 70. As discussed above, the interference signal is detected by the photodetector 80, and is then demodulated, processed, and is stored and/or displayed by the image processor 30.

The apparatus and methods according to embodiments of the present invention collect only imaging information that is important to making a particular medical diagnosis and eliminate the rest of the data. This discussion is provided using as an example a blood vessel, or other body tissue or organ, as the sample, in the case of imaging for the purpose of making a medical diagnosis. The invention would have numerous other applications where selective collection of image data or a reduction in the collected image data is desirable or advantageous.

The approach according to the present invention is to start the collection of each image line of the image at the point of interest in the anatomy, for example, instead of at the probe interface as in conventional intravascular ultrasound (IVUS) systems. This effectively eliminates the time spent collecting data where no diagnostic information exists. For example, this eliminated area could correspond to the lumen of, for example, a blood vessel. As a result, high frame rates can be achieved with good image quality because the time is spent collecting photons from only the areas of diagnostic importance.

The point of interest in a sample that starts an image line can be determined in a number of ways. In the case where the source arm is provided in the form of a probe and the sample, or the target tissue is a blood vessel or portion of a blood vessel, the inner boundary of the blood vessel could be automatically detected, or detected by, or with the help of, an operator, and the reference arm could be adjusted to start the scan at that boundary of the blood vessel or portion of the blood vessel. Referring to FIGS. 2A and 2B, in this case, the image would start at the surface 3, instead of at the outer circumference 56a of the probe assembly 56. The resulting scan or image would be an annulus, as shown in FIG. 2B, that has an inner radius near the inner vessel surface 3 and an outer radius that corresponds to the penetration depth 2 of the imaging system, or the depth of the maximum throw on a reference arm galvanometer.

Since in general, the probe assembly is not exactly in the center of a perfectly round lumen, as shown in FIG. 2C, a distance d from an outer circumference 56a of the probe assembly and the inner circumference 3a of the vessel wall is not a constant as the probe assembly rotates. Therefore, the displayed image of the vessel wall would be eccentric. Furthermore, it would no longer be possible to start the scan at a simple predetermined location from the tip of the probe assembly and large amounts of unnecessary data would be collected. However, as detailed below, it is possible to describe this varying distance with analytic functions.

Alternately, it is possible to describe this varying distance with look-up tables accessed, for example, by a controller, for example, a control computer. The use of look-up tables would allow even more complicated inner surfaces to be detected, such as the one shown in FIG. 2D, and those tracked in U.S. Pat. Nos. 5,195,521 and 6,106,465, which are hereby incorporated by reference. An analog or digital circuit can be designed to adjust the distance offset continually over the scanning of a frame, where a frame corresponds to a complete circumferential sweep of the lumen wall.

In an OCT system, the distance offset is accomplished by varying the length of the reference arm of an optical combiner, such as reference arm 60 and optical combiner 70 shown in FIG. 1. The probe assembly 56 comprises the sample arm or part of the sample arm, such as sample arm 50 in FIG. 1. This distance offset is separate and distinct from the high frequency repetitive optical length variation of the reference arm used to accomplish the depth scanning in OCT. The distance offset has an eccentric or irregular shape, as detailed below, and follows a once-per-frame cycle whereas the scan length variation has a regular shape (typically saw toothed, triangular or sinusoidal) and occurs on a once-per-line rate. A typical OCT image contains up to several hundreds of lines per frame. To obtain an image where data is concentrated in the vessel wall as described above, the distance offset variation must be combined with the scan length variation.

In conventional OCT systems, the reference arm distance offset is typically adjusted once to match the fixed length of the sample and reference arms. Thereafter, the scan length variation is used to create the image. Therefore, there is a need in the art for determining the required distance offset as a function of probe rotation angle, for controlling the reference arm length in a once per frame cycle, and for combining or cooperatively coupling this length variation with the scan length variation.

For example, the distance offset adjustment could be done by moving a reflector, such as a mirror, on a galvanometer with a frequency response in the 1 to 30 of Hertz range, corresponding to the imaging frame rate.

An example of an OCT system according to an embodiment of the present invention capable of such a distance offset adjustment is shown in FIG. 3. The OCT system of FIG. 3 is similar to the OCT system of FIG. 1 and like description is not repeated.

The embodiment of FIG. 3 includes interferometer 69 which includes a sample optical path and a reference optical path together with an optical combiner 70. The sample optical path includes the path traveled by a portion of photons from the optical source 20 along the first optical path 55A through optical combiner 70 (which serves as both a splitter and combiner), then along the first optical path 55B through a scanning mechanism 51 to sample 1, for example, tissue, then back along first optical path 55A through optical combiner 70 along the second optical path 65B to detector 80. The reference optical path includes the path traveled by a second portion of photons from optical source 20 along the first optical path 55A through optical combiner 70, then along the second optical path 65A to reference reflector 64, then back along the second optical path 65A through optical combiner 70 along the second optical path 65B to detector 80.

The sample optical path, combiner 70, and reference optical path make up an interferometer. It should be understood that the sample optical path and the reference optical path may be any combination of elements including fibers, waveguides or free space transmission that yields two optical paths of an interferometer.

The embodiment of FIG. 3 further includes reflector 64 mounted on a scanning mechanism 95, for example, a high speed scanning mechanism such as a galvanometer, or rotating cam as in U.S. Pat. No. 6,191,862. The OCT system of FIG. 3 further includes a controller 98, and a starting point adjustment device 90. The controller 98 and starting point adjustment device may communicate with each other and/or with the image processor and/or other components of the system via path 67A, 67B.

The starting point adjustment device 90 may include software and processing hardware capable of cooperatively functioning with a scanning mechanism 95 in such a way that the OCT system of FIG. 3 only collects data or only processes data after the scanning mechanism 95 passes a starting point. Hence, the OCT only collects and utilizes data that is relevant to the measurement at hand. Alternatively, the starting point adjustment device 90 in cooperation with the controller 98 may function to only actually scan the relevant ranges determined by the starting point adjustment device 90. In either case, the result is that the OCT of FIG. 3 is not burdened by unwanted or unnecessary data and the loss of time (and photons) spent collecting it.

Further, the starting point adjustment device 90 may include a scanning mechanism 90A incorporated therein, whose movement is represented by the arrow C in FIG. 3A, which would adjust the starting point at which data is collected and/or utilized.

An example of an OCT system according to another embodiment of the present invention is shown in FIG. 3B. The OCT system of FIG. 3B is similar to the OCT systems of FIGS. 3 and 3A; however, it additionally comprises a boundary detector 40, for example, a joystick, mouse or rollerball, and a corresponding controller. The boundary detector allows a user to input a boundary of the sample 1.

In one implementation of a method according to the present invention, the boundary detector 40 could be employed to correct the eccentricity of the image manually when the probe assembly 56 is located off-center in a vessel lumen. To accomplish this correction, the operator would move a cursor to the center of the vessel, a cardioid is calculated corresponding to the position and distance to the original center, the amplitude and baseline of a cardioid-shaped waveform is then applied to the starting point adjustment device 90. This would allow the user to effectively center and create a symmetrical, round annulus by simply moving a cursor, for example, a joystick and joystick controller to the actual center of the vessel lumen.

In accordance with another implementation of a method according to the present invention, the controller 98 contains hardware and/or software configured to implement the invention, which detects both the internal window reflection from the probe assembly, as well as the inner wall of the blood vessel. These are the brightest reflections in the OCT image and can be separated from other features. The controller 98 then draws a best fit circle (via a least squares routine or similar technique) to each circle, determines the corresponding center of each, and then determines the required movement to make the two circles concentric.

The controller 98 according to one embodiment of the invention can comprise a lumen detector or indicator component 44, a z-Axis Adjustment lookup table (LUT) 41, a scan converter 42, and a scan conversion LUT 43. As shown in FIG. 4, the hardware and/or software is in communication with the starting point adjustment device 90.

The lumen detector or indicator 44 either automatically detects the first inner wall of the lumen using an algorithm or allows the user to locate the perimeter of the lumen manually via boundary detector 40 (see FIG. 3B). The lumen could be indicated with either a circle of adjustable diameter and center or a freehand trace.

The Z-axis adjustment LUT 41 is a lookup table that has an entry for each scan line in the image. The entry indicates the starting point of the valid data in the image in distance from the probe assembly. The start of valid data is slightly closer to the probe assembly than the first lumen edge according to a preferred embodiment of the invention. The units can be in "virtual samples" (i.e., sample periods) or physical distance such as millimeters or microns. This lookup table is generated from the output of the lumen detector or indicator and downloaded to a waveform generator (not shown) of the starting point adjustment device 90.

The scan conversion LUT 43 is a lookup table that has an entry for each pixel in the scan-converted image. The entry has several fields which may include the scan line number(s) and virtual sample number(s) for the sample point(s) to be interpolated. Any number of sample points can be used to interpolate each output pixel; a typical implementation is to use the four sample points surrounding the output pixel. Furthermore, implementations other than a lookup table can be used to generate the information required for interpolation, such as those taught in U.S. Pat. Nos. 4,468,747 and 4,471,449, which are hereby incorporated by reference.

The scan converter 42 interpolates all the pixels in the output image using a scan converter algorithm, thereby filling in all of the pixels in a rectilinear display from the raw data points in an angle and radius format. For each output pixel, the corresponding entry in the scan conversion lookup table is used to determine the scan line number(s) and virtual sample number(s) to use for the interpolation. The virtual sample number is converted to a physical sample number by subtracting the proper entry in the Z-axis adjustment lookup table (LUG). The proper entry in the Z-axis LUT is found by using the scan line as an index into the table. The physical sample number is then used to fetch the appropriate raw data samples stored in the raw data buffer for interpolation. The physical sample number must be range-checked to ensure that it falls within the limits of the raw data buffer. If the physical sample number is within the allowable range, the interpolation proceeds normally and a value for the output pixel is generated. If not, the output pixel falls outside the image and the interpolation is terminated.

Once the centers of the probe assembly and arterial lumens are determined as described earlier, the required correction can be calculated and implemented. Referring to FIG. 5 and the discussion below, a simple set of equations can be written that determine the reference arm offset as a function of probe assembly rotation angle. The start point adjustment device then creates a variable delay, for example, by driving the reflector, that is added to the reference arm, or alternatively, to the sample arm to modulate the start point of the image line as a function of angle. Alternatively, an optical delay line may be provided, alone or in addition to the start point adjustment device, which creates the variable delay that is added to the reference arm, or alternatively, to the sample arm to modulate the start point of the image line as a function of angle. Other delay techniques may be also utilized, including but not limited to those disclosed in U.S. Pat. Nos. 5,956,355, 6,111,645 and 6,191,862, which are hereby incorporated by reference.

In FIG. 5, $C_p$ is the center of the probe assembly 56, $C_1$ the center of the lumen, c is the distance between centers, $P_1$ is the point being scanned, d is the distance to the point $P_1$ from the center of the probe assembly $C_p$, $\theta$ is the angle measured from the line connecting the centers $C_1$ and $C_p$ to the line connecting the point $P_1$ and the center $C_p$ of the probe assembly 56, b is the radius of the best-fit circle to the arterial lumen at the point $P_1$ being scanned, and $\phi$ is the angle between the line connecting the point $P_1$ and the center $C_1$ of the lumen and the line connecting the centers $C_1$ and $C_p$. The optical probe body is shown as a circle of radius a around point $C_p$. To determine d, and hence the correction factor needed, simple trigonometric relations can be used to arrive at the following:

$$\phi = \cos^{-1}\left(\frac{b^2 + a^2 - d^2}{2cb}\right) \quad (1)$$

$$d = \frac{\sin\varphi}{\sin\theta} b \quad (2)$$

These equations (1) and (2) can be solved iteratively to arrive at the values for d and $\phi$. Once d is known, the reference arm offset can be applied.

An additional advantage of the invention is that it could reduce the required depth scan range to be just approximately 1 or 2 mm. This corresponds to the penetration depth of the OCT beam in a typical highly scattering tissue. Such systems would have an increased signal-to-noise ratio, at a given frame and line rate, by virtue of collecting photons from only approximately 1 or 2 mm of scan depth rather than a more typical 4 mm.

A further advantage is that the system would compensate for respiratory motion, that causes the tissue of interest in surgical microscopy move in and out of the viewing field. In such applications instead of an annular image, the image could be a rectangle or a rectangle with an irregular top surface where the first air-tissue interface is detected.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. A system for performing optical imaging on a sample, comprising:

an optical radiation source;

a sample arm terminating in a probe assembly, the probe assembly comprising a first scanning mechanism that controls the transverse or angular position on a sample at which imaging is performed, the sample position being selectively varied by the first scanning mechanism to scan a sample in at least one transverse or angular dimension;

a reference arm comprising a reference optical reflector;

a first optical path optically coupling the optical radiation source to the probe assembly and a second optical path optically coupling the optical radiation source to the reflector, the optical source applying optical radiation through the first optical path and the probe assembly to a sample and through the second optical path to the reflector;

a second scanning mechanism that determines a longitudinal range relative to the probe assembly from which imaging information is obtained;

a starting point adjustment device that determines a point with respect to a sample at which imaging information collection is to be started;

a controller that controls the second scanning mechanism, wherein imaging information is obtained only from a longitudinal range that contains a selective portion of a sample from which it is desired that imaging information be obtained;

an optical combiner that combines reflections from the sample received through the first optical path and reflections from the reflector received through the second optical path, the resulting combined optical output having optical interference fringes;

a detector that detects the output; and a processor that processes the detected output to obtain a selected image of the sample.

2. The system according to claim 1, further comprising:
a boundary detector that detects a boundary of the sample, wherein in response to an output of the boundary detector, the starting point adjustment device determines a point with respect to a sample at which imaging information is collected.

3. The system according to claim 2, wherein a starting point of each image line of an image is at or near a boundary of the sample.

4. The system according to claim 2, wherein the sample is a vessel and the starting point of each image line of an image is at or near the vessel wall.

5. The system according to claim 2, wherein the starting point adjustment device corrects the eccentricity of the image when the probe assembly is located off-center in a vessel lumen.

6. The system according to claim 5, wherein the boundary detector is a manual input device that allows a user to input a closest edge of the sample with respect to the probe assembly.

7. The system according to claim 6, wherein the manual input device comprises at least one of a joy stick, mouse and rollerball, and a corresponding controller.

8. The system according to claim 6, wherein the second scanning mechanism comprises a galvanometer to which the reflector is attached, wherein the correction is accomplished by adjusting the amplitude and baseline of a cardioid-shaped waveform applied to the galvanometer according to a position an operator enters.

9. The system according to claim 8, wherein the starting point adjustment device determines both an internal window reflection from the probe assembly as well as the inner radius of the sample, draws a best fit circle to each, then determines a required movement to make the two circles concentric, thereby determining the amplitude and offset of a required cardioid.

10. The system according to claim 9, wherein the galvanometer drives the reflector to create a slowly varying delay that is varying substantially cyclically each frame and is added to a second reference arm delay that is varying substantially cyclically each line.

11. The system according to claim 2, wherein the second scanning mechanism comprises a galvanometer to which the reflector is attached, wherein the starting point adjustment device dynamically controls the inner radius or start point of each image line via the galvanometer by adjusting the reference arm on a per cycle or frame basis.

12. The system according to claim 2, wherein the starting point adjustment device comprises an optical delay line, the starting point adjustment device dynamically controlling the inner radius or starting point of each image line via the optical delay line by adjusting the reference arm on a per cycle or frame basis.

13. The system according to claim 12, wherein the second scanning mechanism drives the reflector to create a slowly varying delay that is varying substantially cyclically each frame and is added to a second reference arm delay that is substantially cyclically each line.

14. The system according to claim 12, wherein the system is a microscopy optic coherence tomography system and the point with respect to a sample at which imaging information is collected is at or near the sample surface.

15. The system according to claim 2, wherein a variable starting point of each image line of an image is used to compensate for at least one of patient respiratory motion, cardiac motion, muscle tremors, and variations in the distance to the surface of the sample.

16. The system according to claim 1, wherein the starting point adjustment device corrects the eccentricity of the image when the probe assembly is located off-center in a vessel lumen.

17. The system according to claim 1, wherein the system produces a substantially annular image whose inner radius starts beyond an outer radius of the probe assembly.

18. The system according to claim 17, wherein the inner radius starts at a predetermined depth in the scan.

19. The system according to claim 17, wherein the image has a variable radius as a function of angle.

20. The system according to claim 17, wherein the sample is a vessel and the inner radius or start point of each image line is at or near the vessel wall.

21. The system according to claim 1, wherein the longitudinal range comprises a range starting beyond an outer radius of the probe assembly and extending to a maximum image depth or less capable by the optical imaging system.

22. The system according to claim 1, wherein the longitudinal range comprises a range starting substantially before or at a boundary of the sample and extending to a maximum image depth or less capable by the optical imaging system.

23. The system according to claim 1, wherein the starting point adjustment device comprises a third scanning mechanism, the starting point adjustment device dynamically controlling the inner radius or starting point of each image line via the third scanning mechanism by adjusting the reference arm on a per cycle or frame basis.

24. The system according to claim 23, wherein the third scanning mechanism comprises a galvanometer.

25. A method for performing optical imaging on a sample using an optical imaging device comprising an optical radiation source; a sample arm terminating in a probe assembly, the probe assembly comprising a first scanning mechanism that controls the transverse or angular position on a sample at which imaging is performed, the sample position being selectively varied by the first scanning mechanism to scan a sample in at least one transverse or angular dimension; a reference arm comprising a reference optical reflector; a first optical path optically coupling the optical radiation source to the probe assembly and a second optical path optically coupling the optical radiation source to the reflector, the optical source applying optical radiation through the first optical path and the probe assembly to a sample and through the second optical path to the reflector; a second scanning mechanism that determines a longitudinal range with respect to a sample from which imaging information is obtained; an optical combiner that combines reflections from the sample received through the first optical path and reflections from the reflector received through the second optical path, the resulting combined optical output having optical interference fringes; a detector that detects the output; and a processor that processes the detected output to obtain a selected image of the sample, the method comprising:

determining a longitudinal range containing a selective portion of a sample from which it is desired that imaging information be obtained; and controlling the second scanning mechanism to obtain imaging information only from the determined longitudinal range.

26. The method according to claim 25, wherein the longitudinal range comprises a range starting beyond an outer radius of the probe assembly and extending to a maximum image depth or less capable by the optical imaging system.

27. The method according to claim 25, wherein the longitudinal range comprises a range starting substantially before or at a boundary of the sample and extending to a maximum image depth capable by the optical imaging system.

28. The method according to claim 27, wherein the boundary of the sample is input by a user via a manual input device.

29. The method according to claim 27, wherein the boundary of the sample is detected by a controller.

30. A system for performing optical imaging on a sample, comprising:

an optical radiation source;

a sample arm terminating in a probe assembly, the probe assembly comprising a first scanning mechanism that controls the transverse or angular position on a sample at which imaging is performed, the sample position being selectively varied by the first scanning mechanism to scan a sample in at least one transverse or angular dimension;

a first optical path optically coupling the optical radiation source to the probe and a second optical path optically coupling the optical radiation source to a reflector, the optical source applying optical radiation through the first optical path and the probe assembly to a sample and through the second optical path to the reflector;

a second scanning mechanism that determines a longitudinal range relative to the probe assembly from which imaging information is obtained;

a controller that controls the second scanning mechanism to obtain imaging information from a longitudinal range from which it is desired that imaging information be obtained;

a start point adjustment device that determines a point with respect to a sample at which collected imaging information will be utilized;

an optical combiner that combines reflections from the sample received through the first optical path and reflections from the reflector received through the second optical path, the resulting combined optical output having optical interference fringes;

a detector that detects the output; and a processor that processes the detected output to obtain a selected image of the sample.

31. A system for collecting position data of a sample, comprising:

an interferometer that receives optical radiation and having a first optical path and a second optical path, whereby a first portion of said optical radiation travels along the first optical path and a second portion of said optical radiation travels along the second optical path;

an optical path length varying mechanism that varies a length of one of said first and second optical paths;

a detector optically coupled to said interferometer for outputting position data by detecting said first and second portions of said optical radiation after traveling along said first and second optical paths, respectively;

a controller coupled to said optical path length varying mechanism for controlling the optical path length varying mechanism; and a starting point adjustment device coupled to said controller that determines a point with respect to the sample to start collecting the position data.

32. The system according to claim 31, wherein said optical path length varying mechanism comprises a galvanometer.

33. The system according to claim 31, wherein said optical path length varying mechanism comprises a variable optical delay line.

34. The system according to claim 31, wherein said first optical path comprises a sample arm terminating in a probe assembly.

35. The system according to claim 34, wherein said probe assembly comprises a transverse or angular scanning mechanism for scanning in at least one transverse or angular dimension.

36. The system according to claim 34, wherein said probe assembly comprises a scanning mechanism.

37. The system according to claim 31, wherein said detector outputs imaging information.

38. The system according to claim 31, wherein said second optical path comprises a reference arm terminating in a reference optical reflector.

* * * * *